(12) United States Patent
Naumann et al.

(10) Patent No.: US 6,736,862 B2
(45) Date of Patent: May 18, 2004

(54) INDOLE/INDOLINE BASED HYBRID DYES AND INDOLE/INDOLINE BASED HYBRID DYE INTERMEDIATE PRODUCTS

(75) Inventors: Frank Naumann, Duesseldorf (DE); Detlef Hollenberg, Erkrath (DE); Horst Hoeffkes, Duesseldorf (DE); David Rose, Hilden (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 10/616,428

(22) Filed: Jul. 9, 2003

(65) Prior Publication Data

US 2004/0006834 A1 Jan. 15, 2004

Related U.S. Application Data

(63) Continuation of application No. PCT/EP02/00013, filed on Jan. 3, 2002.

(51) Int. Cl.$^7$ ................................................. A61K 7/13
(52) U.S. Cl. ...................... 8/405; 8/406; 8/410; 8/412; 8/423; 8/455; 8/568; 8/688
(58) Field of Search ........................... 8/405, 406, 410, 8/412, 423, 455, 568, 688

(56) References Cited

U.S. PATENT DOCUMENTS

| | | | | |
|---|---|---|---|---|
| 3,861,868 A | 1/1975 | Milbrada | ....................... | 8/10.2 |
| 4,003,699 A | 1/1977 | Rose et al. | .................... | 8/10.2 |
| 4,865,774 A | 9/1989 | Fabry et al. | ................. | 252/254 |
| 4,931,519 A | 6/1990 | Schenker et al. | ............ | 252/551 |
| 4,961,754 A | * 10/1990 | Grollier | .......................... | 8/423 |
| 5,061,289 A | 10/1991 | Clausen et al. | ................ | 8/405 |
| 5,294,726 A | 3/1994 | Behler et al. | .................. | 554/98 |
| 5,380,340 A | 1/1995 | Neunhoeffer et al. | ........... | 8/409 |
| 5,534,267 A | 7/1996 | Neunhoeffer et al. | ..... | 424/371.4 |
| 5,663,366 A | 9/1997 | Neunheoffer et al. | ..... | 548/371.4 |
| 5,766,576 A | 6/1998 | Lowe et al. | ................... | 424/62 |
| 5,785,717 A | 7/1998 | Manubru et al. | .............. | 8/409 |
| 6,099,592 A | 8/2000 | Vidal et al. | .................... | 8/409 |
| 6,139,589 A | 10/2000 | Vidal et al. | .................... | 8/409 |
| 6,165,229 A | 12/2000 | Vidal et al. | .................... | 8/409 |
| 6,179,882 B1 | 1/2001 | Vidal et al. | .................... | 8/409 |
| 6,210,447 B1 | 4/2001 | Vidal et al. | .................... | 8/409 |
| 6,284,003 B1 | 9/2001 | Rose et al. | .................... | 8/412 |
| 6,340,372 B1 | 1/2002 | Vidal et al. | .................... | 8/409 |
| 6,503,283 B1 | 1/2003 | Lang et al. | .................... | 8/407 |

FOREIGN PATENT DOCUMENTS

| | | |
|---|---|---|
| CA | 2 066 226 | 3/1991 |
| CA | 2 083 378 | 11/1991 |
| DE | 2 215 303 | 10/1972 |
| DE | 23 59 399 A1 | 6/1975 |
| DE | 27 16 671 A1 | 10/1978 |
| DE | 37 23 354 A1 | 1/1989 |
| DE | 37 25 030 A1 | 2/1989 |
| DE | 38 43 892 A1 | 6/1990 |
| DE | 39 26 344 A1 | 2/1991 |
| DE | 39 29 973 A1 | 3/1991 |
| DE | 41 33 957 A1 | 4/1993 |
| DE | 195 43 988 A1 | 5/1997 |
| EP | 0 530 229 B1 | 6/1995 |
| EP | 0 740 931 B1 | 8/1997 |
| EP | 0 740 741 B2 | 10/1998 |
| GB | 1 026 978 | 4/1966 |
| GB | 1 153 196 | 5/1969 |
| JP | 02-19576 | 1/1990 |
| WO | WO 94/08969 A1 | 4/1994 |
| WO | WO94/08970 A1 | 4/1994 |
| WO | WO 96/15765 A1 | 5/1996 |
| WO | WO 07/35553 A1 | 10/1997 |
| WO | WO 97/35550 A1 | 10/1997 |
| WO | WO 97/35552 A1 | 10/1997 |
| WO | WO 98/08485 A1 | 3/1998 |
| WO | WO 98/08486 A2 | 3/1998 |
| WO | WO99/20234 A1 | 4/1999 |

OTHER PUBLICATIONS

The Science of Hair Care, Chapter 7, pp. 235–261, published in Vol. 7 of *Dermatology*, Marcel Dekker Inc. NY/Basle (1986).

The Science of Hair Care, Chapter 8, pp. 263–286, published in vol. 7 of *Dermatology*, Marcel Dekker Inc. NY/Basle (1986).

EU Inventory of Cosmetic Ingredients, Colipa, Mar. 1996 on diskette.

B. Umbach, Kosmetik, $2^{nd}$ Edition, Georg Theime Verlag, Stuttgart New York (1995).

K. Schrader, Grundlagen un Rezepfuren der Kosmetika [Bases and Formulations Cosmetics], $2^{nd}$ Edition, Huethig Buch Verlag, Heidelberg, Germany (1989).

* cited by examiner

Primary Examiner—Brian P. Mruk
Assistant Examiner—Eisa Elhilo
(74) Attorney, Agent, or Firm—Stephen D. Harper; Gregory M. Hill

(57) ABSTRACT

A composition and method for using the composition for dyeing keratin fibers. The composition consists of indole/indoline hybrid dyes and hybrid dye precursors. More particularly, the indole/indoline hybrid dyes and hybrid dye precursors correspond to formula (I):

$$X-S-Y \qquad (I)$$

where
X is a group derived from an indole or indoline derivative as a melanin precursor,
Y is a group derived from
an oxidation dye precursor of the secondary or primary intermediate type or
an indole or indoline derivative as a melanin precursor; and
S is a structural element which is common constituent of the groups X and Y, a direct bond or at least one spacer group. The composition may also be used to color human skin.

10 Claims, No Drawings

INDOLE/INDOLINE BASED HYBRID DYES AND INDOLE/INDOLINE BASED HYBRID DYE INTERMEDIATE PRODUCTS

CROSS REFERENCE TO RELATED APPLICATIONS

This application is a continuation under 35 USC 365(c) and 35 USC 120 of international application PCT/EP02/00013, filed on Jan. 3, 2002, the international application not being published in English. This application also claims priority under 35 USC 119 to DE 101 00 938.0, filed on Jan. 10, 2001.

This invention relates to new indole/indoline hybrid dyes and hybrid dye precursors which are particularly suitable for coloring keratin fibers, to the use of these dyes and dye precursors and to colorants containing these dyes and/or dye precursors.

BACKGROUND OF THE INVENTION

Among the various products available for the cosmetic treatment of the human body, formulations for modifying or shading the color of the hair occupy a prominent position. Disregarding blonding preparations which lighten the hair oxidatively by degrading the natural hair dyes, three types of colorants have long been of importance in the coloring of hair:

So-called oxidation colorants are used for permanent, intensive colors with corresponding fastness properties. Oxidation colorants normally contain oxidation dye precursors, so-called primary intermediates and secondary intermediates. The primary intermediates form the actual dyes with one another or by coupling with one or more secondary intermediates under the influence of oxidizing agents or atmospheric oxygen.

Colorants or tints containing substantive dyes as their coloring component are normally used for temporary colors. Substantive dyes are based on dye molecules which are directly absorbed onto the hair and do not require an oxidative process for developing the color. Dyes such as these include, for example, henna which has been used since ancient times for coloring the body and hair.

In recent years, a new coloring process has received considerable attention. In this process, precursors of the natural hair dye, melanin, more particularly derivatives of indole or indoline, are applied to the hair and then form virtually "nature-identical" dyes in the hair in the course of oxidative processes. One such process using 5,6-dihydroxyindolines as the dye precursors is described in EP-B1 530 229. If preparations containing 5,6-dihydroxyindoline are applied, in particular repeatedly, people with gray hair can be given back their natural hair color. Color development can be carried out with atmospheric oxygen as sole oxidizing agent so that no other oxidizing agent has to be used.

Although it is possible in principle to formulate colorants containing only a dye or a dye precursor, such colorants are of only limited significance in practice with the exception of a few products which contain melanin precursors for example.

Instead, commercial hair coloring products normally contain a mixture of about 3 to 8 different dyes and/or dye precursors. However, the individual dyes generally differ in their capacity to be absorbed onto the hair and in their fastness to light, perspiration, rubbing and washing which, in addition, can be determined to a considerable extent by the structural properties and condition of the hair. These differences are pronounced above all when substantive dyes are used for adjusting the shade in oxidation hair colorants, as has hitherto been essential for many shades.

Accordingly, there is often a need in the development of new hair colorants to carry out extensive tests not only to obtain certain shades, but above all to ensure that the color is stable for the required period both in regard to shade and in regard to intensity.

SUMMARY OF THE INVENTION

It has now surprisingly been found that many of the problems mentioned above can be completely or at least partly avoided by the use of substances which possess both the properties of a melanin precursor and the properties of an oxidation dye precursor or any other melanin precursor. In particular, it has been found that the dyes have a very high capacity for absorption onto the hair comparable with that of known hair dyes or hair dye precursors and lead to brilliant intensive hair colors. By virtue of the molecular linkage, the problem of differing fastness properties of the two dyes or dye precursors can thus largely be overcome in many cases.

Substances such as these usable in hair colorants, which are referred to hereinafter as "hybrid dyes", are new.

DETAILED DESCRIPTION OF THE INVENTION

In a first embodiment, therefore, the present invention relates to indole/indoline hybrid dyes and hybrid dye precursors, more particularly for coloring keratin fibers, which correspond to formula (I):

$$X-S-Y \qquad (I)$$

where
- X is a group derived from an indole or indoline derivative as a melanin precursor,
- Y is a group derived from
  - an oxidation dye precursor of the secondary or primary intermediate type or
  - an indole or indoline derivative as a melanin precursor; and
- S is a structural element which is common constituent of the groups X and Y, a direct bond or at least one spacer group.

The compounds corresponding to formula (I) are obtainable by standard synthesis methods of organic chemistry. In this connection, reference is specifically made to the Synthesis Examples in the following.

As mentioned above, the structural principles of known classes of dyes form the basis of the newly developed hybrid dyes.

The group X is derived from a precursor of melanin selected from the derivatives of indole and indoline. In the context of the present invention, "precursors of melanin" are understood to be derivatives of indole and indoline which are capable of forming melanin dyes or corresponding melanin dye derivatives in an oxidative process.

According to the invention, the groups X in this embodiment are derived from indoles and indolines which contain at least one hydroxy and/or amino group, preferably as a substituent on the six-membered ring. These groups may carry other substituents, for example in the form of etherification or esterification of the hydroxy group or alkylation of the amino group. Indoles and indolines containing two of these groups, particularly two hydroxy groups, of which one or both may be etherified or esterified are particularly preferred.

According to the invention, particularly preferred groups X are derived from derivatives of indoline, such as 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 5-hydroxyindoline, 6-hydroxyindoline, 5-aminoindoline, 6-aminoindoline and 4-aminoindoline.

Most particularly preferred groups X are derivatives of 5,6-dihydroxyindoline corresponding to formula (IIa):

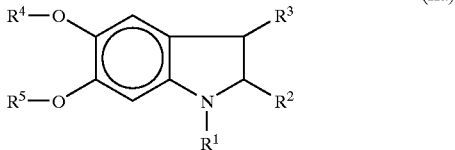

(IIa)

in which—independently of one another $R^1$ is hydrogen, a $C_{1-4}$ alkyl group, a $C_{1-4}$ hydroxyalkyl group, a $C_{3-6}$ cycloalkyl group, a vinyl group or an allyl group, $R^2$ is hydrogen or a —COOH group which may even be present as a salt with a physiologically compatible cation, $R^3$ is hydrogen or a $C_{1-4}$ alkyl group, $R^4$ is hydrogen, a $C_{1-4}$ alkyl group or a group —CO—$R^6$ where $R^6$ is a $C_{1-4}$ alkyl group or an optionally substituted phenyl group and $R^5$ stands for one of the groups mentioned for $R^4$.

According to the invention, preferred representatives are 5,6-dihydroxyindoline, N-methyl-5,6-dihydroxyindoline, N-ethyl-5,6-dihydroxy-indoline, N-propyl-5,6-dihydroxyindoline, N-butyl-5,6-dihydroxyindoline. The parent compound, 5,6-dihydroxyindoline, is most particularly preferred.

According to the invention, preferred indoles from which the group X is derived are 5,6-dihydroxyindole, N-methyl-5,6-dihydroxyindole, N-ethyl-5,6-dihydroxy-indole, N-propyl-5,6-dihydroxyindole, N-butyl-5,6-dihydroxyindole, 5,6-dihydroxyindole-2-carboxylic acid, 5-hydroxyindole, 6-hydroxyindole, 5-aminoindole, 6-aminoindole and 4-aminoindole.

Particular preference is attributed to derivatives of 5,6-dihydroxyindole corresponding to formula (IIb):

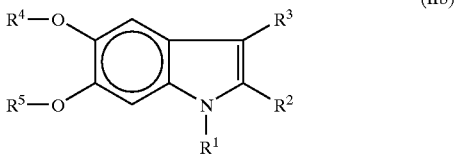

(IIb)

in which—independently of one another $R^1$ is hydrogen, a $C_{1-4}$ alkyl group, a $C_{1-4}$ hydroxyalkyl group, a $C_{3-6}$ cycloalkyl group, a vinyl group or allyl group, $R^2$ is hydrogen or a —COOH group which may even be present as a salt with a physiologically compatible cation, $R^3$ is hydrogen, a $C_{1-4}$ alkyl group or a group —CH$_2$—NR$^7$R$^8$, where $R^7$ and $R^8$ independently of one another are hydrogen or a $C_{1-4}$ alkyl group, $R^4$ is hydrogen, a $C_{1-4}$ alkyl group or a group —CO—$R^6$ where $R^6$ is a $C_{1-4}$ alkyl group or an optionally substituted phenyl group and $R^5$ stands for one of the groups mentioned for $R^4$.

According to the invention, preferred representatives are 5,6-dihydroxyindole, N-methyl-5,6-dihydroxyindole, N-ethyl-5,6-dihydroxy-indole, N-propyl-5,6-dihydroxyindole, N-butyl-5,6-dihydroxyindole. The parent compound, 5,6-dihydroxyindole, is most particularly preferred.

The group Y is a group derived from an oxidation dye precursor of the secondary or primary intermediate type or an indole or indoline derivative as a melanin precursor.

In a first preferred embodiment of the present invention, the group Y derives from an oxidation dye precursor of the secondary intermediate type.

m-Phenylenediamine derivatives, naphthols, resorcinol and resorcinol derivatives, pyrazolones and m-aminophenol derivatives are generally used as secondary intermediates.

Preferred classes of oxidation dye precursors of the secondary intermediate type from which the group Y may be derived are:

3-Aminophenol and derivatives thereof; Preferred representatives are 5-amino-2-methylphenol, 5-(3-hydroxypropylamino)-2-methylphenol, 3-amino-2-chloro-6-methyl-phenol, 2-hydroxy-4-aminophenoxyethanol, 3-amino-6-methoxy-2-methylaminophenol, 2,6-dimethyl-3-aminophenol, 3-trifluoroacetyl-amino-2-chloro-6-methylphenol, 5-amino-4-chloro-2-methylphenol, 5-amino-4-methoxy-2-methyl-phenol, 5-(2'-hydroxyethyl)-amino-2-methylphenol, 3-dimethylaminophenol, 3-diethylaminophenol, N-cyclopentyl-3-aminophenol, 1,3-dihydroxy-5-(methylamino)-benzene, 3-ethylamino-4-methylphenol and 2,4-dichloro-3-aminophenol;

2-Aminophenol and derivatives thereof;

1,3-Diaminobenzene and derivatives thereof; Preferred representatives are 2,4-diaminophenoxyethanol, 1,3-bis-(2,4-diaminophenoxy)-propane, 1-methoxy-2-amino-4-(2'-hydroxy-ethylamino)-benzene, 1,3-bis-(2,4-diaminophenyl)-propane, 2,6-bis-(2-hydroxyethylamino)-1-methylbenzene, 1-amino-3-bis-(2-hydroxy-ethyl)-aminobenzene, 1,2-bis-(2,4-diaminophenoxy)-benzene and 1,3-bis-(2,4-diaminophenoxy)-benzene;

1,2-Diaminobenzene and derivatives thereof; Preferred representatives are 3,4-diaminobenzoic acid and 2,3-diamino-1-methylbenzene;

Di- and trihydroxybenzenes and derivatives thereof; Preferred representatives are resorcinol, resorcinol monomethyl ether, 2-methyl resorcinol, 5-methyl resorcinol, 2,5-dimethyl resorcinol, 2-chlororesorcinol, 4-chlororesorcinol, pyrogallol and 1,2,4-trihydroxybenzene and also resorcinol dimethyl ether;

Pyridine derivatives; Preferred representatives are 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-3,4-diaminopyridine, 2,6-dihydroxy-4-methylpyridine, 2,6-diaminopyridine, 2,3-diamino-6-methoxypyridine and 3,5-diamino-2,6-dimethoxypyridine;

Naphthalene derivatives; Preferred representatives are 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxy-naphthalene, 1,8-dihydroxynaphthalene, 2,7-dihydroxynaphthalene and 2,3-dihydroxynaphthalene and also 1-aminonaphthalene;

Morpholine derivatives; Preferred representatives are 6-hydroxybenzomorpholine and 6-aminobenzomorpholine;

Quinoxaline derivatives; A preferred representative is 6-methyl-1,2,3,4-tetrahydroquinoxaline;

Pyrazole derivatives; A preferred representative is 1-phenyl-3-methylpyrazol-5-one;

Indole derivatives; Preferred representatives are 4-hydroxyindole, 6-hydroxyindole and 7-hydroxyindole;

Methylenedioxybenzene derivatives; Preferred representatives are 3,4-methylenedioxyphenol, 1-amino-3,4-methylenedioxybenzene and 1-(2'-hydroxyethyl)-amino-3,4-methylenedioxybenzene;

Pyrimidine derivatives; Preferred representatives are 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine;

Heterocyclic compounds as disclosed in WO 97/35550, WO 97/35552, WO 97/35553, WO 98/08485 and WO 98/08486, to which reference is expressly made.

Particularly preferred secondary intermediates are 3-aminophenol, 5-amino-2-methylphenol, 2,4-dichloro-3-aminophenol, 2-chloro-6-methyl-3-aminophenol, 2-methyl-4-chloro-5-aminophenol, 1,3-phenylenediamine, 1,3-bis-(2',4'-diaminophenoxy)-propane, resorcinol, resorcinol monomethyl ether, 2-methylresorcinol, 5-methylresorcinol, 2,5-dimethylresorcinol, 2-chlororesorcinol, 4-chlororesorcinol, 1-naphthol, 1,5-, 2,7- and 1,7-dihydroxynaphthalene, 1-phenyl-3-methylpyrazol-5-one, 2-amino-3-hydroxypyridine and 2,6-dihydroxy-3,4-dimethylpyridine.

With regard to other oxidation dye precursors of the secondary intermediate type substantive dyes from which the group Y may be derived, reference is also specifically made to the known reference books, for example Ch. Zviak, The Science of Hair Care, Chapter 8 (pages 264–267), published as Vol. 7 of the Series "Dermatology" (Editors: Ch. Culnan and H. Maibach), Marcel Dekker Inc., New York/Basel, 1986 and to the "Europäische Inventar der Kosmetik-Rohstoffe" published by the Europäische Gemeinschaft and available on floppy disk from the Bundesverband Deutscher Industrie-und Handelsunternehmen für Arzneimittel, Reformwaren und Körperpflegemittel e.V., Mannheim, Germany.

In a second preferred embodiment of the present invention, the group Y is derived from an oxidation dye precursor of the primary intermediate type.

The primary intermediates normally used are primary aromatic amines containing another free or substituted hydroxy or amino group in the para or ortho position, diaminopyridine derivatives, heterocyclic hydrazones, 4-aminopyrazole derivatives and 2,4,5,6-tetraaminopyrimidine and derivatives thereof.

Preferred classes of oxidation dye precursors of the primary intermediate type from which the group Y can be derived are:

1,4-Diaminobenzene and derivatives thereof; Preferred representatives are p-phenylenediamine, p-toluylenediamine, 1-(2'-hydroxyethyl)-2,5-diaminobenzene, N,N-bis(2-hydroxyethyl)-p-phenylenediamine, bis-(4-aminophenyl)-amine, 2-(2,5-diaminophenoxy)-ethanol, 1,3-bis-(N-(2-hydroxyethyl)-N-(4-aminophenylamino))-2-propanol, 1,10-bis-(2,5-diaminophenyl)-1,4,7,10-tetraoxadecane and N,N'-bis-(4'-aminophenyl)-1,4-diazacycloheptane and corresponding compounds with one or more halogen atoms, more particularly chlorine and fluorine, on the benzene ring;

1,2-Diaminobenzene and derivatives thereof;

1,2,4-Triaminobenzene and derivatives thereof;

4-Aminopenol and derivatives thereof; Preferred representatives are p-aminophenol, 2-chloro-4-aminophenol, 4-amino-3-methylphenol, 2-hydroxyethylamino-4-aminophenol, 4-amino-3-fluorophenol, 2-aminomethyl-4-aminophenol, 2-hydroxymethyl-4-aminophenol, 4-amino-2-((diethylamino)-methyl)-phenol, bis-(2-hydroxy-5-aminophenyl)-methane, 4-amino-2-(2-hydroxyethoxy)-phenol;

2-Aminophenol and derivatives thereof; Preferred representatives are o-aminophenol and 2-amino-5-methylphenol;

Diaminopyridine derivatives; Preferred representatives are 2,5-diaminopyridine, 2,5-diamino-4-methylpyridine, 2,5-diamino-4,6-dimethylpyridine;

Triaminopyridine derivatives; A preferred representative is 2,3,5-triaminopyridine;

Heterocyclic hydrazones;

4-Aminopyrazole derivatives; Preferred representatives are 4,5-diamino-1,3-dimethylpyrazole, 1-phenyl-3-carboxyamido-4-amino-5-pyrazolone and 4,5-diaminopyrazole derivatives according to EP 0 740 931 or WO 94/08970 such as, for example, 4,5-diamino-1-(2'-hydroxyethyl)-pyrazole and 4,5-diamino-1-(4'-chlorobenzyl)-pyrazole;

Pyrimidine derivatives; Preferred representatives are 2,4,5,6-tetraaminopyrimidine, 2-hydroxy-4,5,6-triaminopyrimidine, 4-hydroxy-2,5,6-triamino-pyrimidine, 2,4-dihydroxy-5,6-diaminopyrimidine and 2-dimethyl-amino-4,5,6-triaminopyrimidine.

Particularly preferred primary intermediates are p-phenylenediamine, p-toluylenediamine, 1,2,4-phenylenetriamine, p-aminophenol, 1-(2'-hydroxyethyl)-2,5-diaminobenzene, N,N-bis-(2'-hydroxyethyl)-p-phenylenediamine, 2-(2',5'-diaminophenyl)-ethanol, N,N'-bis-(2'-hydroxyethyl)-N,N'-bis-(4'-aminophenyl)-1,3-diaminopropan-2-ol, 2-(2',5'-diaminophenoxy)-ethanol, 4-amino-3-methylphenol, 2,5-diaminopyridine, 2,5-diamino-4-methylpyridine, 2,5-diamino-4,6-dimethylpyridine, 2,3,5-triaminopyridine, 2,4,5,6-tetraaminopyrimidine, 2-hydroxy-4,5,6-triaminopyrimidine, 2,4-dihydroxy-5,6-diaminopyrimidine, 4-hydroxy-2,5,6-triaminopyrimidine and 4,5-diamino-1,3-dimethylpyrazole, 4,5-diamino-1-(2'-hydroxyethyl)-pyrazole.

In another preferred embodiment of the invention, the group Y is derived from a primary intermediate in the form of a p-phenylenediamine derivative or one of its physiologically compatible salts. Particularly preferred p-phenylenediamine derivatives correspond to formula (E1):

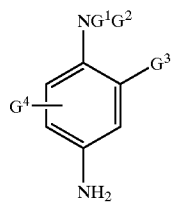

in which
G¹ stands for a hydrogen atom, a $C_{1-4}$ alkyl radical, a $C_{1-4}$ monohydroxyalkyl radical, a $C_{2-4}$ polyhydroxyalkyl radical, a $(C_{1-4})$-alkoxy-$(C_{1-4})$-alkyl radical, a 4'-aminophenyl radical or a $C_{1-4}$ alkyl radical substituted by a nitrogen-containing group, a phenyl group or a 4'-aminophenyl group;

G² stands for a hydrogen atom, a $C_{1-4}$ alkyl radical, a $C_{1-4}$ monohydroxyalkyl radical, a $C_{2-4}$ polyhydroxyalkyl radical, a $(C_{1-4})$-alkoxy-$(C_{1-4})$-alkyl radical or a $C_{1-4}$ alkyl radical substituted by a nitrogen-containing group;

G³ stands for a hydrogen atom, a halogen atom, such as a chlorine, bromine, iodine or fluorine atom, a $C_{1-4}$ alkyl radical, a $C_{1-4}$ monohydroxyalkyl radical, a $C_{2-4}$ polyhydroxyalkyl radical, a $C_{1-4}$ hydroxyalkoxy radical, a $C_{1-4}$ acetylaminoalkoxy radical, a $C_{1-4}$ mesylaminoalkoxy radical or a $C_{1-4}$ carbamoylaminoalkoxy radical;

G⁴ is a hydrogen atom, a halogen atom or a $C_{1-4}$ alkyl radical or if G³ and G⁴ are in the ortho position to one another, they may together form a bridging α,ω-alkylenedioxo group such as, for example, an ethylenedioxy group.

Examples of the $C_{1-4}$ alkyl radicals mentioned as substituents in the compounds according to the invention are the methyl, ethyl, propyl, isopropyl and butyl groups. Ethyl and methyl radicals are preferred alkyl radicals. According to the invention, preferred $C_{1-4}$ alkoxy radicals are, for example, methoxy or ethoxy radicals. Other preferred examples of a $C_{1-4}$ hydroxyalkyl group are a hydroxymethyl, a 2-hydroxyethyl, a 3-hydroxypropyl or a 4-hydroxybutyl group. A 2-hydroxyethyl group is particularly preferred. One example of a $C_{2-4}$ polyhydroxyalkyl group is 1,2-dihydroxyethyl. According to the invention, examples of halogen atoms are F, Cl or Br atoms. Cl atoms are most particularly preferred. According to the invention, the other terms used are derived from the definitions given here. Examples of nitrogen-containing groups corresponding to formula (II) are, in particular, the amino groups, $C_{1-4}$ monoalkylamino groups, $C_{1-4}$ dialkylamino groups, $C_{1-4}$ trialkylammonium groups, $C_{1-4}$ monohydroxyalkylamino groups, imidazolinium and ammonium.

Particularly preferred p-phenylenediamines corresponding to formula (E1) are selected from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)-aniline, N,N-bis-(β-hydroxyethyl)-p-phenylenediamine, 4-N,N-bis-(β-hydroxyethyl)-amino-2-methylaniline, 4-N,N-bis-(β-hydroxyethyl)-amino-2-chloroaniline, 2-(β-hydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl-β-hydroxyethyl)-p-phenylene-diamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine and 5,8-diaminobenzo-1,4-dioxane and physiologically compatible salts thereof.

According to the invention, most particularly preferred p-phenylenediamine derivatives corresponding to formula (E1) are p-phenylenediamine, p-toluylenediamine, 2-(β-hydroxyethyl)-p-phenylenediamine and N,N-bis-(β-hydroxyethyl)-p-phenylenediamine.

In another preferred embodiment of the invention, the group Y is derived from a primary intermediate in the form of a compound containing at least two aromatic nuclei substituted by amino and/or hydroxyl groups.

These binuclear primary intermediates include in particular compounds corresponding to formula (E2) below and physiologically compatible salts thereof:

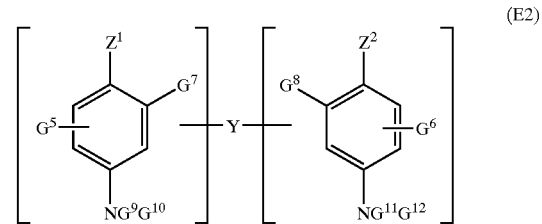

in which
Z¹ and Z² independently of one another stand for a hydroxyl or $NH_2$ radical which is optionally substituted by a $C_{1-4}$ alkyl radical, by a $C_{1-4}$ hydroxyalkyl radical and/or by a bridging group Y or which is optionally part of a bridging ring system, the bridging group Y is a $C_{1-4}$ alkylene group such as, for example, a linear or branched alkylene chain or an alkylene ring which may be interrupted or terminated by one or more nitrogen-containing groups and/or one or more hetero atoms, such as oxygen, sulfur or nitrogen atoms, and may optionally be substituted by one or more hydroxyl or $C_{1-8}$ alkoxy radicals, or a direct bond, G⁵ and G⁶ independently of one another stand for a hydrogen or halogen atom, a $C_{1-4}$ alkyl radical, a $C_{1-4}$ monohydroxyalkyl radical, a $C_{2-4}$ polyhydroxyalkyl radical, a $C_{1-4}$ aminoalkyl radical or a direct bond to the bridging group Y, G⁷, G⁸, G⁹, G¹⁰, G¹¹ and G¹² independently of one another stand for a hydrogen atom, a direct bond to the bridging group Y or a $C_{1-4}$ alkyl radical, with the provisos that
the compounds of formula (E2) contain only one bridging group Y per molecule and
the compounds of formula (E2) contain at least one amino group which carries at least one hydrogen atom.

According to the invention, the substituents used in formula (E2) are as defined in the foregoing.

Preferred binuclear primary intermediates corresponding to formula (E2) are, in particular, N,N'-bis-(β-hydroxyethyl)-N,N'-bis-(4'-aminophenyl)-1,3-diaminopropanol, N,N'-bis-(β-hydroxyethyl)-N,N'-bis-(4'- aminophenyl)-ethylenediamine, N,N'-bis-(4-aminophenyl)-tetramethylene diamine, N,N'-bis-(β-hydroxyethyl)-N,N'-bis-(4'-aminophenyl)-tetramethylene diamine, N,N'-bis-(4-methylaminophenyl)-tetramethylene diamine, N,N'-bis-(ethyl)-N,N'-bis-(4'-amino-3'-methylphenyl)-ethylene diamine, bis-(2-hydroxy-5-aminophenyl)-methane, N,N'-bis-(4'-aminophenyl)-1,4-diazacycloheptane, N,N'-bis-(2-hydroxy-5-aminobenzyl)-piperazine, N-(4'-aminophenyl)-p-phenylenediamine and 1,10-bis-(2',5'-diaminophenyl)-1,4,7,10-tetraoxadecane and physiologically compatible salts thereof.

Most particularly preferred binuclear primary intermediates corresponding to formula (E2) are N,N'-bis-(β-hydroxyethyl)-N,N'-bis-(4'-aminophenyl)-1,3-diaminopropanol, bis-(2-hydroxy-5-aminophenyl)-methane, N,N'-bis-(4'-aminophenyl)-1,4-diazacycloheptane and 1,10-bis-(2',5'-diaminophenyl)-1,4,7,10-tetraoxadecane or one of their physiologically compatible salts.

In another preferred embodiment of the invention, the group Y is derived from a primary intermediate in the form of a p-aminophenol derivative or a physiologically compatible salt thereof. Particularly preferred p-aminophenol derivatives correspond to formula (E3):

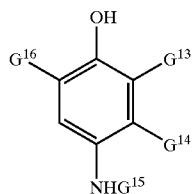
(E3)

in which
G$^{13}$ stands for a hydrogen atom, a halogen atom, a C$_{1-4}$ alkyl radical, a C$_{1-4}$ monohydroxyalkyl radical, a C$_{2-4}$ polyhydroxyalkyl radical, a (C$_{1-4}$)-alkoxy-(C$_{1-4}$)-alkyl radical, a C$_{1-4}$ aminoalkyl radical, a hydroxy-(C$_{1-4}$)-alkylamino radical, a C$_{1-4}$ hydroxyalkyoxy radical, a C$_{1-4}$ hydroxyalkyl-(C$_{1-4}$)-aminoalkyl radical or a (di-C$_{1-4}$-alkylamino)-(C$_{1-4}$)-alkyl radical, G$^{14}$ stands for a hydrogen atom or a halogen atom, a C$_{1-4}$ alkyl radical, a C$_{1-4}$ monohydroxyalkyl radical, a C$_{2-4}$ polyhydroxyalkyl radical, a (C$_{1-4}$)-alkoxy-(C$_{1-4}$)-alkyl radical, a C$_{1-4}$ aminoalkyl radical or a C$_{1-4}$ cyanoalkyl radical, G$^{15}$ stands for hydrogen, a C$_{1-4}$ alkyl radical, a C$_{1-4}$ monohydroxyalkyl radical, a C$_{2-4}$ polyhydroxyalkyl radical, a phenyl radical or a benzyl radical and G$^{16}$ stands for hydrogen or a halogen atom.

According to the invention, the substituents used in formula (E3) are defined as in the foregoing.

Preferred p-aminophenols corresponding to formula (E3) are, in particular, p-aminophenol, N-methyl-p-aminophenol, 4-amino-3-methylphenol 4-amino-3-fluorophenol, 2-hydroxymethylamino-4-aminophenol, 4-amino-3-hydroxymethylphenol, 4-amino-2-(β-hydroxyethoxy)-phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)-phenol, 4-amino-2-fluorophenol, 4-amino-2-chlorophenol, 4-amino-2,6-dichlorophenol, 4-amino-2-(diethylaminomethyl)-phenol and physiologically compatible salts thereof.

Most particularly preferred compounds corresponding to formula (E3) are p-aminophenol, 4-amino-3-methylphenol, 4-amino-2-aminomethylphenol and 4-amino-2-(diethylaminomethyl)-phenol.

The primary intermediate may also be selected from o-aminophenol and its derivatives such as, for example, 2-amino-4-methylphenol, 2-amino-4-chlorophenol or 2-amino-5-methylphenol.

In addition, the group Y may be derived from a heterocyclic primary intermediate such as, for example, pyridine, pyrimidine, pyrazole, pyrazole/pyrimidine derivatives and physiologially compatible salts thereof.

Preferred pyridine derivatives are, in particular, the compounds described in GB 1,026,978 and GB 1,153,196, such as 2,5-diaminopridine, 2-(4'-methoxyphenyl)-amino-3-aminopyridine, 2,3-diamino-6-methoxy-pyridine, 2-(β-methoxyethyl)-amino-3-amino-6-methoxypyridine and 3,4-diaminopyridine.

Preferred pyrimidine derivatives are, in particular, the compounds described in DE 2359399, JP 02019576 A2 and WO 96/15765, such as 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyridine.

Preferred pyrazole derivatives are, in particular, the compounds described in DE 3843892, DE 4133957, WO 94/08969, WO 94/08970, EP 740931 and DE 19543988, such as 4,5-diamino-1-methylpyrazole, 4,5-diamino-1-(β-hydroxyethyl)-pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl pyrazole, 4,5-diamino-3-tert.butyl-1-methylpyrazole, 4,5-diamino-1-tert.butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(β-aminoethyl)-amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)-amino-1-methylpyrazole.

Preferred pyrazole-pyrimidine derivatives are, in particular, the derivatives of pyrazole-[1,5-a]-pyrimidine corresponding to formula (E4) below and tautomeric forms thereof where a tautomeric equilibrium exists:

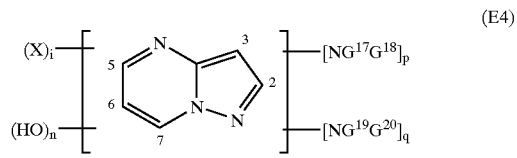
(E4)

in which
G$^{17}$, G$^{18}$, G$^{19}$ and G$^{20}$ independently of one another stand for a hydrogen atom, a C$_{1-4}$ alkyl radical, an aryl radical, a C$_{1-4}$ hydroxyalkyl radical, a C$_{2-4}$ polyhydroxyalkyl radical, a (C$_{1-4}$)-alkoxy-(C$_{1-4}$)-alkyl radical, a C$_{1-4}$ aminoalkyl radical which may optionally be protected by an acetylureide or sulfonyl radical, a (C$_{1-4}$)-alkylamino-(C$_{1-4}$)-alkyl radical, a di[(C$_{1-4}$)-alkyl]-(C$_{1-4}$)-aminoalkyl radical, the dialkyl radicals optionally forming a carbon cycle or a heterocycle with 5 or 6 links, a $C_{1-4}$ hydroxyalkyl or a di-$(C_{1-4})$-[hydroxyalkyl]-$(C_{1-4})$-aminoalkylradical;

the X radicals independently of one another stand for a hydrogen atom, a $C_{1-4}$ alkyl radical, an aryl radical, a $C_{1-4}$ hydroxyalkyl radical, a $C_{2-4}$ polyhydroxyalkyl radical, a $C_{1-4}$ aminoalkyl radical, a $(C_{1-4})$-alkylamino-$(C_{1-4})$-alkyl radical, a di[$(C_{1-4})$-alkyl]-$(C_{1-4})$-aminoalkyl radical, the dialkyl radicals optionally forming a carbon cycle or a heterocycle with 5 or 6 links, a $C_{1-4}$ hydroxyalkyl or a di-$(C_{1-4})$[hydroxyalkyl]-$(C_{1-4})$-aminoalkyl radical, an amino radical, a $C_{1-4}$ alkyl or a di-$(C_{1-4}$ hydroxyalkyl)-amino radical, a halogen atom, a carboxylic acid group or a sulfonic acid group, i has the value 0, 1, 2 or 3, p has the value 0 or 1, q has the value 0 or 1 and n has the value 0 or 1, with the proviso that the sum of p+q is not 0, where p+q=2, n has the value 0 and the groups $NG^{17}G^{18}$ and $NG^{19}G^{20}$ occupy the (2,3); (5,6); (6,7); (3,5) or (3,7) positions;

where p+q=1, n has the value 1 and the groups $NG^{17}G^{18}$ (or $NG^{19}G^{20}$) and the group OH occupy the (2,3); (5,6); (6,7); (3,5) or (3,7) positions.

The substituents used in formula (E9) are as defined in the foregoing.

If the pyrazole-[1,5-a]-pyrimidine corresponding to formula (E4) above contains a hydroxy group in one of the positions 2, 5 or 7 of the ring system, a tautomeric equilibrium exists as illustrated, for example, in the following scheme:

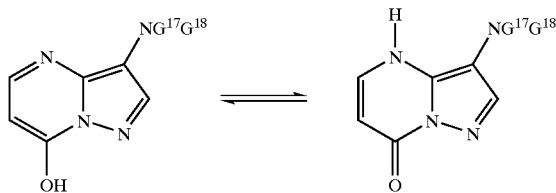

Among the pyrazole-[1,5-a]-pyrimidines corresponding to formula (E4) above, the following may be particularly mentioned:

pyrazole-[1,5-a]-pyrimidine-3,7-diamine;
2,5-dimethylpyrazole-[1,5-a]-pyrimidine-3,7-diamine;
pyrazole-[1,5-a]-pyrimidine-3,5-diamine;
2,7-dimethylpyrazole-[1,5-a]-pyrimidine-3,5-diamine;
3-aminopyrazole-[1,5-a]-pyrimidin-7-ol;
3-aminopyrazole-[1,5-a]-pyrimidin-5-ol;
2-(3-aminopyrazole-[1,5-a]-pyrimidin-7-ylamino)-ethanol;
2-(7-aminopyrazole-[1,5-a]-pyrimidin-3-ylamino)-ethanol;
2-[(3-aminopyrazole-[1,5-a]-pyrimidin-7-yl)-(2-hydroxyethyl)-amino]-ethanol;
2-[(7-aminopyrazole-[1,5-a]-pyrimidin-3-yl)-(2-hydroxyethyl)-amino]-ethanol;
5,6-dimethylpyrazole-[1,5-a]-pyrimidine-3,7-diamine;
2,6-dimethylpyrazole-[1,5-a]-pyrimidine-3,7-diamine;
3-amino-7-dimethylamino-2,5-dimethylpyrazole-[1,5-a]-pyrimidine and physiologically compatible salts thereof and tautomeric forms thereof where a tautomeric equilibrium exists.

The pyrazole-[1,5-a]-pyrimidines corresponding to formula (E4) above may be prepared by cyclization from an aminopyrazole or from hydrazine, as described in the literature.

With regard to other oxidation dye precursors of the secondary intermediate type from which the group Y may be derived, reference is also specifically made to the known reference books, for example Ch. Zviak, The Science of Hair Care, Chapter 8 (pages 264–267), published as Vol. 7 of the Series "Dermatology" (Editors: Ch. Culnan and H. Maibach), Marcel Dekker Inc., New York/Basel, 1986 and to the "Europäische Inventar der Kosmetik-Rohstoffe" published by the Europäische Gemeinschaft and available on floppy disk from the Bundesverband Deutscher Industrie- und Handelsunternehmen für Arzneimittel, Reformwaren und Körperpflegemittel e.V., Mannheim, Germany.

In a third, preferred embodiment of the present invention, the group Y derives from a precursor of melanin selected from indole and indoline derivatives. Suitable and preferred dyes Y are derived in principle from the same compounds that are described in detail above in the definition of the group X.

Although, according to the invention, compounds where the groups X and Y are identical are not intended to be excluded from the defined group of hybrid dyes with the structure (I), the compounds according to this embodiment normally contain different groups X and Y.

The spacer group S of formula (I) may be a structural element which is a common constituent of the groups X and Y. In the most simple case, the structural element is an atom which is a common constituent of the groups X and Y, preferably a C, O, S, N or P atom. In a particularly preferred embodiment, the structural element is an N-containing structural element and, more particularly, an N-containing structural element corresponding to formula (III) which is a common constituent of the group X dervied from indole or indoline derivatives and the group Y derived from aminobenzene or pyrimidine or pyridine derivatives.

Preferably, however, the group S in structural formula (I) is at least one spacer group. Where several, for example two, spacer groups are present, they are—preferably independently of one another—unsubstituted and/or substituted alkylene groups which each terminally attack nitrogen atom (s) of the groups X and Y.

In a third embodiment of the invention, the group S in structural formula (I) stands for a direct bond.

In these cases where the group S in structural formula (I) is a direct bond, the π-electron systems of the groups X and Y will generally interact so that the light absorption behavior of the hybrid dye generally differs distinctly from that of the groups X and Y. As a result, a significantly different color tone is obtained on the hair by comparison with colors formed with a mixture of corresponding dyes which correspond to the groups X and Y.

However, a core object of the present invention is to avoid the problems arising in many areas where complex dye mixtures are used, for example in regard to absorptivity and fastness to washing, without altering either the color tone or the shade.

According to the invention, therefore, it is generally preferred for S to be a spacer group through which no interaction between the π-electron systems of the groups X and Y occurs. Accordingly, S preferably contains at least one carbon atom with $sp^3$ hybridization on the direct connecting line between the groups X and Y.

Where several, for example two, spacer groups are present, they are—preferably independently of one another—unsubstituted and/or substituted alkyl groups which each terminally attack nitrogen atom(s) of the groups X and Y.

Preferred spacer groups S are:

Alkylene groups corresponding to the general formula —$C_nH_{2n}$—, more particularly —$(CH_2)_n$—, in which n is an integer, preferably a number of 1 to 8 and more particularly a number of 1 to 4; According to the invention, preferred alkylene groups are the methylene, 1,2-ethylene and 1,3-propylene group;

Cycloaliphatic groups, such as cyclopentyl, cyclohexyl and cycloheptyl groups;

Mono- and polyhydroxyalkylene groups corresponding to the general formula —$C_nH_{2n-x}(OH)_x$—, in which n is an integer, preferably a number of 1 to 8 and more particularly a number of 1 to 4 and x is an integer, more particularly a number of 1 to 3; Preferred hydroxyalkylene groups are the hydroxymethylene, hydroxy-1,2-ethylene, 2-hydroxy-1,3-propylene, 2,3-dihydroxy-1,3-propylene and 2,3-dihydroxy-1,4-butylene group;

Dialkyleneamino groups optionally substituted at the alkyl chains, more particularly those corresponding to the general formula —$(CH_2)_n$—N(Z)—$(CH_2)_m$—, in which n and m independently of one another represent an integer of 1 to 8, more particularly 1 to 4, but are preferably the same number, and Z represents hydrogen, a $C_{1-8}$ and more particularly $C_{1-4}$ alkyl group, a $C_{1-8}$ and more particularly $C_{1-4}$ monohydroxyalkyl group, a $C_{2-8}$ and more particularly $C_{2-4}$ dihydroxyalkyl group or a $C_{3-8}$ and more particularly $C_{3-4}$ trihydroxyalkyl group, and those corresponding to the following general formula:

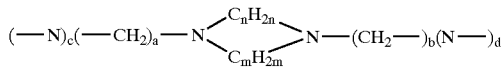

in which a and b independently of one another represent integers of 0 to 4 and c and d stand for 0 or 1, with the proviso that c=0 when a=0 and d=0 when b=0, n is an integer of 1 to 5 and m is an integer of 1 to 3, with the proviso that the sum n+m=3 to 8. The 1,4-piperazino group is particularly preferred;

Trialkylenediamino groups optionally substituted at the alkyl chains, more particularly those corresponding to the general formula: —$(CH_2)_n$—N(Z)—$(CH_2)_m$—N(A)—$(CH_2)_p$—, in which n, m and p independently of one another may represent an integer of 1 to 8 and more particularly 1 to 4, although n and m preferably stand for the same number, and Z and A independently of one another represent hydrogen, a $C_{1-8}$ and more particularly $C_{1-4}$ alkyl group, a $C_{1-8}$ and more particularly $C_{1-4}$ monohydroxyalkyl group, a $C_{2-8}$ and more particularly $C_{2-4}$ dihydroxyalkyl group or a $C_{3-8}$ and more particularly $C_{3-4}$ trihydroxyalkyl group;

Ether groups optionally substituted at the alkyl chains, more particularly those corresponding to the general formula —$(CH_2)_n$—O—$(CH_2)_m$—, in which n and m independently of one another may represent an integer of 1 to 8 and more particularly 1 to 4, but preferably stand for the same number;

Polyether groups optionally substituted at the alkyl chains, more particularly those corresponding to the general formula —$(CH_2)_n$—O—$(CH_2)_m$—O—$(CH_2)_m$—$(CH_2)_n$—, in which n and m independently of one another may represent an integer of 1 to 8 and more particularly 1 to 4, but preferably stand for the same number;

Sulfur-containing groups, more particularly groups corresponding to the general formula —$(CH_2)_n$—$S(O)_o$—$(CH_2)_m$— in which n and m independently of one another may represent an integer of 1 to 8 and more particularly 1 to 4, but preferably stand for the same number, and o is the number 0, 1 or 2.

The spacers S in the hybrid dyes according to the invention are attached by their two free bonds to the groups X and Y so that they each replace a hydrogen atom as substituent in the dye or dye precursor molecules on which the groups X and Y are based.

In a first preferred embodiment, the spacer group replaces a hydrogen atom directly attached to a ring system of the group X or Y as substituent. Examples of such ring systems are aromatic and cycloaliphatic hydrocarbon ring systems, more particularly benzene, naphthalene, anthracene, naphthoquinone and anthraquinone systems heterocyclic ring systems, more particularly pyridine, pyrazole, pyrimidine, indole and indoline systems.

In a second preferred embodiment, the spacer group S replaces a hydrogen atom of a primary or secondary amino group attached to an aromatic, cycloaliphatic or heterocyclic ring system either directly or through an aliphatic hydrocarbon group as substituent.

In a third embodiment, the spacer group S replaces the hydrogen atom of a hydroxy group attached to an aromatic, cycloaliphatic or heterocyclic ring system either directly or through an aliphatic hydrocarbon group as substituent.

Particularly preferred hybrid dyes according to the invention correspond to general formula (III), where X is derived from indole or indoline derivatives as melanin precursors and Y is derived from aminobenzene or pyridine derivatives and S is a structural element containing a N atom which is a common constituent of the groups X and Y:

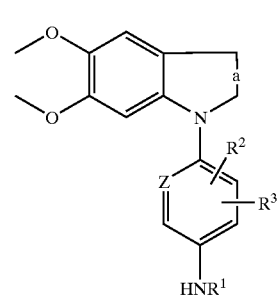

(III)

where $R^1$ is H, $C_{1-4}$ alkyl, $C_{2-4}$ alkenyl, $C_{1-4}$ hydroxyalkyl or $C_{2-4}$ polyhydroxyalkyl and $R^2$ and $R^3$ are the same or independently of one another represent H, $C_{1-4}$ alkyl, halogen, $C_{1-4}$ alkoxy, amino-$C_{1-4}$-alkyl or $N(R^1)_2$, Z stands for CH or N and a is a single or double bond. The following compounds, for example, are particularly preferred:

|  | $R^1$ | $R^2$ | $R^3$ | Z | a |
|---|---|---|---|---|---|
| III a | H | H | H | CH | Single |
| III b | H | H | H | N | Single |

The hybrid dyes according to the invention are eminently suitable for coloring keratin fibers. Keratin fibers in the context of the invention are pelts, wool, feathers and in particular human hair. However, there is nothing to prevent them being used in other fields, particularly color photography.

Accordingly, in a second embodiment, the present invention relates to compositions for coloring keratin fibers, more particularly human hair, which contain a hybrid dye corresponding to structural formula (I). The teaching according to the invention does of course also encompass compositions containing combinations of more than one hybrid dye corresponding to formula (I).

The compositions according to the invention for coloring human hair may also contain any of the ingredients typical of such compositions.

The compositions according to the invention contain the hybrid dyes corresponding to formula (I) in quantities of normally 0.01% by weight to 10% by weight, preferably 0.05% by weight to 5% by weight and more particularly 0.1% by weight to 3% by weight, based on the colorant as a whole.

The colorants according to the invention preferably contain at least one other dye, one other dye precursor and/or an indole or indoline derivative as melanin precursor.

In a first embodiment, colorants which contain at least one oxidation dye precursor besides a hybrid dye of formula (I) are particularly preferred. These oxidation dye precursors may be both of the secondary intermediate type and of the primary intermediate type.

Suitable oxidation dye precursors of the primary intermediate type are, for example, primary aromatic amines with another free or substituted hydroxy or amino group in the para or ortho position, diaminopyridine derivatives, heterocyclic hydrazones, 4-aminopyrazole derivatives and 2,4,5,6-tetraaminopyimidine and derivatives thereof.

According to the invention, preferred classes of primary intermediates are:

1,4-Diaminobenzene and derivatives thereof; Preferred representatives are p-phenylenediamine, p-toluylenediamine, 1-(2'-hydroxyethyl)-2,5-diaminobenzene, N,N-bis-(2-hydroxyethyl)-p-phenylenediamine, bis-(4-aminophenyl)-amine, 2-(2,5-diaminophenoxy)-ethanol, 1,3-bis-(N-(2-hydroxyethyl)-N-(4-aminophenylamino))-2-propanol, 1,10-bis-(2,5-diaminophenyl)-1,4,7,10-tetraoxadecane and N,N'-bis-(4'-aminophenyl)-1,4-diazacycloheptane and corresponding compounds with one or more halogen atoms, more particularly chlorine and fluorine, on the benzene ring;

1,2-Diaminobenzene and derivatives thereof;

1,2,4-Triaminobenzene and derivatives thereof;

4-Aminopenol and derivatives thereof; Preferred representatives are p-aminophenol, 2-chloro-4-aminophenol, 4-amino-3-methylphenol, 2-hydroxyethylamino-4-aminophenol, 4-amino-3-fluorophenol, 2-aminomethyl-4-aminophenol, 2-hydroxymethyl-4-aminophenol, 4-amino-2-((diethylamino)-methyl)-phenol, bis-(2-hydroxy-5-aminophenyl)-methane, 4-amino-2-(2-hydroxyethoxy)-phenol;

2-Aminophenol and derivatives thereof; A preferred representative is o-aminophenol;

Diaminopyridine derivatives; Preferred representatives are 2,5-diaminopyridine, 2,5-diamino-4-methylpyridine, 2,5-diamino-3-methyleneamino-4,6-dimethylpyridine;

Triaminopyridine derivatives; A preferred representative is 2,3,5-triaminopyridine;

Heterocyclic hydrazones;

4-Aminopyrazole derivatives; Preferred representatives are 4,5-diamino-1,3-dimethylpyrazole, 1-phenyl-3-carboxyamido-4-amino-5-pyrazolone and 4,5-diaminopyrazole derivatives according to EP 0 740 931 or WO 94/08970 such as, for example, 4,5-diamino-1-(2'-hydroxyethyl)-pyrazole and 4,5-diamino-1-(4'-chlorobenzyl)-pyrazole;

Pyrimidine derivatives; Preferred representatives are 2,4,5,6-tetraaminopyrimidine, 2-hydroxy-4,5,6-triaminopyrimidine, 4-hydroxy-2,5,6-triaminopyrimidine, 2,4-dihydroxy-5,6-diaminopyrimidine and 2-dimethylamino-4,5,6-triaminopyrimidine.

Particularly preferred primary intermediates or substances are those corresponding to the above formulae E1, E2, E3 and E4 and, more particularly, p-phenylenediamine, p-toluylenediamine, 1,2,4-phenylenetriamine, p-aminophenol, 1-(2'-hydroxyethyl)-2,5-diaminobenzene, N,N-bis-(2'-hydroxyethyl)-p-phenylenediamine, 2-(2',5'-diaminophenyl)-ethanol, N,N'-bis-(2'-hydroxyethyl)-N,N'-bis-(4'-aminophenyl)-1,3-diaminopropan-2-ol, 2-(2',5'-diaminophenoxy)-ethanol, 4-amino-3-methylphenol, 4-amino-2-((diethylamino)-methyl)-phenol, 2-aminomethyl-4-aminophenol, 2,5-diaminopyridine, 2,5-diamino-4-methylpyridine, 2,5-diamino-3-methyleneamino-4,6-dimethylpyridine, 2,3,5-triaminopyridine, 2,4,5,6-tetraaminopyrimidine, 2-hydroxy-4,5,6-triaminopyrimidine, 2,4-dihydroxy-5,6-diaminopyrimidine, 4-hydroxy-2,5,6-triaminopyrimidine and 4,5-diamino-1,3-dimethylpyrazole, 4,5-diamino-1-(2'-hydroxyethyl)-pyrazole.

Suitable oxidation dye precursors of the secondary intermediate type are, for example, m-phenylenediamine derivatives, naphthols, resorcinol and resorcinol derivatives, pyrazolones and m-aminophenol derivatives.

According to the invention, preferred classes of secondary intermediates are:

3-Aminophenol and derivatives thereof; Preferred representatives are 5-amino-2-methylphenol, 5-(3-hydroxypropylamino)-2-methylphenol, 3-amino-2-chloro-6-methylphenol, 2-hydroxy-4-aminophenoxyethanol, 3-amino-6-methoxy-2-methylaminophenol, 2,6-dimethyl-3-aminophenol, 3-trifluoroacetyl-amino-2-chloro-6-methylphenol, 5-amino-4-chloro-2-methylphenol, 5-amino-4-methoxy-2-methyl-phenol, 5-(2'-hydroxyethyl)-amino-2-methylphenol, 3-dimethylaminophenol, 3-diethylaminophenol, N-cyclopentyl-3-aminophenol, 1,3-dihydroxy-5-(methylamino)-benzene, 3-ethylamino-4-methylphenol and 2,4-dichloro-3-aminophenol;

2-Aminophenol and derivatives thereof;

1,3-Diaminobenzene and derivatives thereof; Preferred representatives are 2,4-diaminophenoxyethanol, 1,3-bis-(2,4-diaminophenoxy)-propane, 1-methoxy-2-amino-4-(2-hydroxy-ethylamino)-benzene, 1,3-bis-(2,4-diaminophenyl)-propane, 2,6-bis-(2-hydroxyethylamino)-1-methylbenzene, 1-amino-3-bis-(2-hydroxy-ethyl)-aminobenzene, 1,2-bis-(2,4-diaminophenoxy)-benzene and 1,3-bis-(2,4-diaminophenoxy)-benzene;

1,2-Diaminobenzene and derivatives thereof; Preferred representatives are 3,4-diaminobenzoic acid and 2,3-diamino-1-methylbenzene;

Di- and trihydroxybenzenes and derivatives thereof; Preferred representatives are resorcinol, resorcinol monomethyl ether, 2-methyl resorcinol, 5-methyl resorcinol, 2,5-dimethyl resorcinol, 2-chlororesorcinol, 4-chlororesorcinol, pyrogallol and 1,2,4-trihydroxybenzene and also resorcinol dimethyl ether;

Pyridine derivatives; Preferred representatives are 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-3,4-diaminopyridine, 2,6-dihydroxy-4-methylpyridine, 2,6-diaminopyridine, 2,3-diamino-6-methoxypyridine and 3,5-diamino-2,6-dimethoxypyridine;

Naphthalene derivatives; Preferred representatives are 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxy-naphthalene, 1,8-dihydroxynaphthalene, 2,7-dihydroxynaphthalene and 2,3-dihydroxynaphthalene and also 1-aminonaphthalene;

Morpholine derivatives; Preferred representatives are 6-hydroxybenzomorpholine and 6-aminobenzomorpholine;

Quinoxaline derivatives; A preferred representative is 6-methyl-1,2,3,4-tetrahydroquinoxaline;

Pyrazole derivatives; A preferred representative is 1-phenyl-3-methylpyrazol-5-one;

Indole derivatives; Preferred representatives are 4-hydroxyindole, 6-hydroxyindole and 7-hydroxyindole;

Methylenedioxybenzene derivatives; Preferred representatives are 3,4-methylenedioxyphenol, 1-amino-3,4-methylenedioxybenzene and 1-(2'-hydroxyethyl)-amino-3,4-methylenedioxybenzene;

Pyrimidine derivatives; Preferred representatives are 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine;

Heterocyclic compounds as disclosed in WO 97/35550, WO 97/35552, WO 97/35553, WO 98/08485 and WO 98/08486, to which reference is expressly made.

Particularly preferred secondary intermediates are 3-aminophenol, 5-amino-2-methylphenol, 2,4-dichloro-3-aminophenol, 2-chloro-6-methyl-3-aminophenol, 2-methyl-4-chloro-5-aminophenol, 1,3-phenylenediamine, 1,3-bis-(2', 4'-diaminophenoxy)-propane, resorcinol, resorcinol monomethyl ether, 2-methylresorcinol, 5-methylresorcinol, 2,5-dimethylresorcinol, 2-chlororesorcinol, 4-chlororesorcinol, 1-naphthol, 1,5-, 2,7- and 1,7-dihydroxynaphthalene, 1-phenyl-3-methylpyrazol-5-one, 2-amino-3-hydroxypyridine and 2,6-dihydroxy-3,4-dimethylpyridine.

In this embodiment, it can be preferred
to use a hybrid dye of formula (I) containing a group Y derived from an oxidation dye precursor of the secondary intermediate type in combination with at least one other oxidation dye precursor of the primary intermediate type,
to use a hybrid dye of formula (I) containing a group Y derived from an oxidation dye precursor of the primary intermediate type in combination with at least one other oxidation dye precursor of the secondary intermediate type to use a hybrid dye of formula (I) containing a group Y derived from a derivative of indole or indoline as a melanin precursor in combination with at least one other oxidation dye precursor of the secondary intermediate type.

The compositions according to the invention contain the other oxidation dye precursors of the secondary intermediate and primary intermediate types in quantities of normally 0.01% by weight to 10% by weight, preferably 0.05% by weight to 5% by weight and more particularly 0.1 % by weight to 3% by weight, based on the colorant as a whole.

In a second embodiment, preferred colorants contain at least one substantive dye in addition to a hybrid dye of formula (I).

Substantive dyes suitable for use in accordance with the invention are, for example, nitrophenytlenediamines, nitroaminophenols, azo dyes, anthraquinones and indophenols. Preferred substantive dyes are the compounds known under the International names or commercial names of HC Yellow 2, HC Yellow 4, HC Yellow 5, HC Yellow 6, Basic Yellow 57, Disperse Orange 3, HC Red 1, HC Red 3, HC Red 13, HC Red BN, Basic Red 76, HC Blue 2, HC Blue 12, Disperse Blue 3, Basic Blue 7, Basic Blue 26, Basic Blue 99, HC Violet 1, Disperse Violet 1, Disperse Violet 4, Basic Violet 2, Basic Violet 14, Acid Violet 43, Disperse Black 9 Acid Black 52, Basic Brown 16 and Basic Brown 17 and also 1,4-bis-(β-hydroxyethyl)-amino-2-nitrobenzene, 3-nitro-4-(β-hydroxyethyl)-aminophenol, 4-amino-2-nitrodiphenylamine-2'-carboxylic acid, 6-nitro-1,2,3,4-tetrahydroquinoxaline, 2-hydroxy-1,4-naphthoquinone, 1-(2'-hydroxyethyl)-amino-4-methyl-2-nitrobenzene, picramic acid, 2-amino-6-chloro-4-nitrophenol, 4-ethylamino-3-nitrobenzoic acid and 2-chloro-6-ethylamino-1-hydroxy-4-nitrobenzene. The cationic substantive dyes marked under the name of Arianor® are particularly preferred substantive dyes.

The compositions according to the invention may also contain naturally occurring dyes such as, for example, henna red, henna neutral, henna black camomile blossom, sandalwood, black tea, black alder bark, sage, logwood, madder root, catechu, sedre and alkanet.

The compositions according to the invention of this embodiment contain the substantive dyes in a quantity of preferably 0.01 to 20% by weight, based on the colorant as a whole.

In a third embodiment, colorants which contain at least one derivative of indole or indoline as a melanin precursor in addition to a hybrid dye of formula (I) are particularly preferred.

According to the invention, preferred indoles and indolines are those which contain at least one hydroxy and/or amino group, preferably as a substituent on the six-membered ring. These groups may carry other substituents, for example in the form of etherification or esterification of the hydroxy group or alkylation of the amino group. Compounds containing two of these groups, particularly two hydroxy groups, of which one or both may be etherified or esterified are particularly preferred.

According to the invention, particularly preferred dye precursors are derivatives of indoline, such as 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 5-hydroxyindoline 6-hydroxyindoline, 5-aminoindoline, 6-aminoindoline and 4-aminoindoline.

Most particularly preferred dye precursors are derivatives of 5,6-dihydroxyindoline corresponding to formula (IVa):

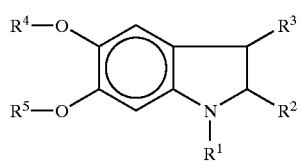

(IVa)

in which—independently of one another
- $R^1$ is hydrogen, a $C_{1-4}$ alkyl group, a $C_{1-4}$ hydroxyalkyl group or a $C_{3-6}$ cycloalkyl group, a vinyl group or an allyl group,
- $R^2$ is hydrogen or a —COOH group which may even be present as a salt with a physiologically compatible cation,
- $R^3$ is hydrogen or a $C_{1-4}$ alkyl group,
- $R^4$ is hydrogen, a $C_{1-4}$ alkyl group or a group —CO—$R^6$ where $R^6$ is a $C_{1-4}$ alkyl group or an optionally substituted phenyl group,
- $R^5$ stands for one of the groups mentioned for $R^4$, or a physiologically compatible salt of these compounds with an organic or inorganic acid.

According to the invention, preferred representatives are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline. The parent compound, 5,6-dihydroxyindoline, is most particularly preferred.

According to the invention, preferred indoles are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 5-hydroxyindole, 6-hydroxyindole, 5-aminoindole, 6-aminoindole and 4-aminoindole.

Particular preference is attributed to derivatives of 5,6-dihydroxyindole corresponding to formula (IVb):

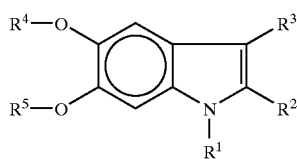

(IVb)

in which—independently of one another
- $R^1$ is hydrogen, a $C_{1-4}$ alkyl group, a $C_{1-4}$ hydroxyalkyl group or a $C_{3-6}$-cycloalkyl group, a vinyl group or an allyl group
- $R^2$ is hydrogen or a —COOH group which may even be present as a salt with a physiologically compatible cation,
- $R^3$ is hydrogen, a $C_{1-4}$ alkyl group or a group —CH$_2$—NR$^7$R$^8$ where $R^7$ and $R^8$ independently of one another represent hydrogen or a $C_{1-4}$ alkyl group,
- $R^4$ is hydrogen, a $C_{1-4}$ alkyl group or a group —CO—$R^6$ where $R^6$ is a $C_{1-4}$ alkyl group or an optionally substituted phenyl group and
- $R^5$ stands for one of the groups mentioned for $R^4$, or a physiologically compatible salt of these compounds with an organic or inorganic acid.

According to the invention, preferred representatives are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole. The parent compound, 5,6-dihydroxyindole, is most particularly preferred.

The indoline and indole derivatives present in the compositions according to the invention may be used both as free bases and in the form of their physiologically compatible salts with inorganic or organic bases, for example hydrochlorides, sulfates and hydrobromides.

The present invention does of course also encompass compositions containing more than one indoline or indole derivative or mixtures of indoline and indole derivatives.

The indole or indoline derivatives are present in the compositions according to the invention in quantities of normally 0.05 to 10% by weight and preferably 0.2 to 5% by weight.

In this embodiment, it may be preferred
- to use a hybrid dye of formula (I) containing a group Y derived from an oxidation dye precursor of the secondary intermediate type in combination with at least one derivative of indole or indoline as a precursor of melanin,
- to use a hybrid dye of formula (I) containing a group Y derived from an oxidation dye precursor of the primary intermediate type in combination with at least one derivative of indole or indoline as a precursor of melanin.

In the embodiments mentioned, the oxidation dye precursors, substantive dyes or melanin precursors do not have to be single compounds. Instead, the hair colorants according to the invention—due to the processes used for producing the individual dyes—may contain small quantities of other components providing they do not adversely affect the coloring result or have to be ruled out for other reasons, for example toxicological reasons.

With regard to the dyes suitable for use in the hair coloring and tinting formulations according to the invention, reference is also specifically made to Ch. Zviak's work The Science of Hair Care, Chapter 7 (pages 248–250; Substantive Dyes) and Chapter 8, pages 264–267; Oxidation Dye Precursors), published as Vol. 7 of the Series "Dermatology" (Editors: Ch. Culnan and H. Maibach), Marcel Dekker Inc., New York/Basel, 1986 and to the "Europäische Inventar der Kosmetik-Rohstoffe" published by the Europäische Gemeinschaft and available on floppy disk from the Bundesverband Deutscher Industrie- und Handelsunternehmen für Arzneimittel, Reformwaren und Körperpflegemittel e.V., Mannheim, Germany.

In a preferred variant of this embodiment, compositions according to the invention containing a hybrid dye of formula (I) in which the groups X and optionally Y derive from a melanin precursor of the indole or indoline type contain no dyes or dye precursors other than the hybrid dyes mentioned.

In another preferred variant, compositions according to the invention containing a hybrid dye of formula (I), in which the groups X and optionally Y derive from a melanin precursor of the indole or indoline type, and/or a melanin precursor additionally contain at least one amino acid or oligopeptide.

Amino acids in the context of the invention are substances which contain at least one amino group and at least one —COOH or —SO$_3$H group.

Preferred amino acids are aminocarboxylic acids, more particularly α-aminocarboxylic acids and ω-aminocarboxylic acids. Among the α-aminocarboxylic acids, arginine, lysine, ornithine and histidine are particularly preferred.

The amino acids are preferably added to the formulations according to the invention in free form. However, the amino acids may also be used in salt form. Preferred salts are the compounds containing hydrohalic acids, more particularly hydrochlorides and hydrobromides.

Particularly preferred amino acids are lysine and particularly arginine used in particular in free form but also as the hydrochloride.

In addition, the amino acids may also be used in the form of oligopeptides and protein hydrolyzates providing steps are taken to ensure that the necessary quantities of compounds conforming to the definition of amino acids according to the invention are present. Reference is expressly made in this connection to the disclosure of DE-OS 22 15 303.

The present invention does of course also encompass compositions containing two or more amino acids or oligopeptides. Combinations of arginine with another amino acid or an oligopeptide are preferred.

The compositions according to the invention contain the amino acid or oligopeptide in quantities of preferably 0.1 to 10% by weight and more preferably 1 to 4% by weight, based on the composition as a whole.

Hair colorants, more particularly those where the color is developed oxidatively with atmospheric oxygen or other oxidizing agents, such as hydrogen peroxide, are normally adjusted to a mildly acidic or alkaline pH value, i.e. to a pH value in the range from about 5 to 11. To this end, the colorants contain alkalizing agents, normally alkali metal or alkaline earth metal hydroxides, ammonia or organic amines.

In one special embodiment of the present invention, the amino acid or the oligopeptide is used not only to intensify color development, but also at least partly as an alkalizing agent. Accordingly, amino acids and oligopeptides of which 2.5% by weight solutions in water have a pH value of 9 or higher are preferably used in this embodiment. Such amino acids are the preferred compounds arginine and lysine. In this particular embodiment, the other alkalizing agent is preferably selected from the group consisting of monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol and triethanolamine and alkali metal and alkaline earth metal hydroxides. Within this group, monoethanolamine, triethanolamine and 2-amino-2-methylpropanol and 2-amino-2-methyl-1,3-propanediol are particularly preferred. ω-Amino acids, such as ω-aminocaproic acid, are also preferably used as alkalizing agents in this embodiment of the invention.

Particularly advantageous properties are exhibited by formulations in which the amino acid or the oligopeptide and the other alkalizing agent are present in a ratio by weight of 1:5 to 5:1. Quantity ratios of 1:2 to 2:1 have proved to be particularly suitable.

To produce the colorants according to the invention, the compulsory and optional constituents mentioned above are incorporated in a suitable—preferably water-containing—carrier. Such carriers are, for example, cremes, emulsions, gels or even surfactant-containing foaming solutions, for example shampoos, foam aerosols or other preparations suitable for application to the hair. These preparations are adjusted to a pH value of preferably 5 to 11 and, more preferably, 7 to 10 with the above-mentioned alkalizing agents or suitable acids such as, in particular, food-grade acids, such as citric acid, tartaric acid, lactic acid and acetic acid.

The colorants according to the invention may also contain any of the known active substances, additives and auxiliaries typical of such preparations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants. Anionic surfactants can be particularly useful.

Suitable anionic surfactants for the hair colorants according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ether, amide and hydroxyl groups and—generally—ester groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear and branched fatty acids containing 8 to 22 carbon atoms (soaps), ether carboxylic acids corresponding to the formula R—O—$(CH_2$—$CH_2O)_x$—$CH_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—$O(CH_2$—$CH_2O)_x$—$SO_3H$, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a $C_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl amino-propionate, cocoacyl aminoethyl aminopropionate and $C_{12-18}$ acyl sarcosine.

Nonionic surfactants contain, for example, a polyol group, a poly-alkylene glycol ether group or a combination of polyol and polyglycol ether groups as the hydrophilic group. Examples of such compounds are products of the addition of 2 to 30 mol ethylene oxide and/or 0 to 5 mol propylene oxide onto linear fatty alcohols containing 8 to 22 carbon atoms, onto fatty acids containing 12 to 22 carbon atoms and onto alkylphenols containing 8 to 15 carbon atoms in the alkyl group, $C_{12-22}$ fatty acid monoesters and diesters of products of the addition of 1 to 30 mol ethylene oxide onto glycerol, $C_{8-22}$ alkyl mono- and oligoglycosides, ethoxylated analogs thereof and esters thereof, for example with tartaric acid and citric acid, products of the addition of 5 to 60 mol ethylene oxide onto castor oil and hydrogenated castor oil, products of the addition of ethylene oxide onto sorbitan fatty acid esters, products of the addition of ethylene oxide onto fatty acid alkanolamides.

Examples of cationic surfactants suitable for use in the hair treatment preparations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethi-cone), Dow Corning 929 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the methyl hydroxyalkyl dialkoyloxyalkyl ammonium methosulfates marketed under the trade name of Stepantex® and the corresponding products commercially available as Dehyquart®, are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

According to the invention, the use of anionic surfactants in combination with zwitterionic surfactants can be particularly preferred.

According to the invention, compositions additionally containing a polymer selected from the group consisting of anionic, zwitterionic, ampholytic, cationic and nonionic polymers are also preferred.

According to the invention, compositions additionally containing a cationic polymer are particularly preferred.

Among the cationic polymers, the permanently cationic polymers are preferred. According to the invention, "permanently cationic polymers" are polymers which contain a cationic group irrespective of the pH of the composition. These are generally polymers which contain a quaternary nitrogen atom, for example in the form of an ammonium group. Preferred cationic polymers are, for example, the quaternized cellulose derivatives commercially available under the names of Celquat® and Polymer JR®. The compounds Celquat® H 100, Celquat® L 200 and Polymer JR® 400 are preferred quaternized cellulose derivatives, polysiloxanes containing quaternary groups such as, for example, the commercially available products Q2-7224 (manufacturer: Dow Corning; a stabilized trimethyl silyl amodimethicone), Dow Corning® 929 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80), cationic guar derivatives such as, in particular, the products marketed under the names of Cosmedia® Guar and Jaguar®, polymeric dimethyl diallyl ammonium salts and copolymers thereof with esters and amides of acrylic acid and methacrylic acid. The products commercially available under the names of Merquat® 100 (poly(dimethyl diallylammonium chloride)) and Merquat® 550 (dimethyl diallylammonium chloride/acrylamide copolymer) are examples of such cationic polymers, copolymers of vinyl pyrrolidone with quaternized derivatives of dialkylaminoacrylate and methacrylate such as, for example, vinyl pyrrolidone/dimethylamino methacrylate copolymers quaternized with diethyl sulfate. Such compounds are commercially available under the name of Gafquat® 734 and Gafquat® 755, The vinyl pyrrolidones/vinyl imidazolinium methochloride copolymers commercially available under the name of Luviquat® FC 370, FC 550, FC 905 and HM 552, quaternized polyvinyl alcohol; and the polymers containing quaternary nitrogen atoms in the main polymer chain known under the names of Polyquaternium 2, Polyquaternium 17, Polyquaternium 18 and Polyquaternium 27.

Other suitable cationic polymers are the polymers known by the names of Polyquaternium-24 (commercial product: Quatrisoft® LM 200 for example), Polyquaternium-32, Polyquaternium-35 and Polyquaternium-37 (commercial products: Salcare® SC 92 and Salcare® SC 95 for example). Also suitable for use in accordance with the invention are the vinyl pyrrolidone copolymers known by the commercial names of Copolymer 845 (manufacturer: ISP), Gaffix® VC 713 (manufacturer: ISP), Gafquat® ASCP 1011, Gafquat® HS 110, Luviquat® 8155 and Luviquat® MS 370.

According to the invention preferred cationic polymers are quaternized cellulose derivatives, polymeric dimethyl diallyl ammonium salts, Polyquaternium-27 and copolymers thereof and polymers of the Polyquaternium-2 type. Cationic cellulose derivatives, more particularly the commercial product Polymer® JR 400, and polymers of the Polyquaternium-2 type, more particularly the commercial product Mirapol® A-15, are most particularly preferred cationic polymers.

The cationic polymers are present in the compositions according to the invention in quantities of preferably 0.05 to 5% by weight, based on the composition as a whole.

In many cases, amphopolymers may also be used as an alternative to the cationic polymers. Amphopolymers are amphoteric polymers, i.e. polymers which contain both free amino groups and free —COOH or —SO$_3$H groups in the molecule and which are capable of forming inner salts, zwitterionic polymers which contain quaternary ammonium groups and —COO⁻ or —SO$_3^-$ groups in the molecule and polymers which contain —COOH— or SO$_3$H groups and quaternary ammonium groups. One example of an amphopolymer suitable for use in accordance with the invention is the acrylate resin commercially available as Amphomer® which is a copolymer of tert.butylaminoethyl methacrylate, N-(1,1,3,3-tetramethylbutyl)-acrylamide and two or more monomers from the group consisting of acrylic acid, methacrylic acid and simple esters thereof. Other preferred amphopolymers consist of unsaturated carboxylic acids (for example acrylic and methacrylic acid), cationically derivatized unsaturated carboxylic acids (for example acrylamidopropyl trimethyl ammonium chloride) and optionally other ionic or nonionic monomers of the type disclosed, for example, in DE-OS 39 29 973 and the prior art literature cited therein. According to the invention, terpolymers of acrylic acid, methyl acrylate and methacrylamidopropyl trimonium chloride, which are commercially available under the name of Merquat® 2001 N, and the commercial product Merquat® 280 may also be used as amphopolymers.

The compositions according to the invention also contain at least one nonionic or anionic polymer with thickening properties, preferably optionally crosslinked polyacrylic acids, cellulose derivatives, for example methyl cellulose, hydroxyalkyl cellulose and carboxymethyl cellulose, and xanthan gum.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, gum arabic, karaya gum, locust bean gum, linseed gums, dextrans, starch fractions and derivatives, such as amylose, amylopectin and dextrins, clays such as, for example, bentonite or fully synthetic hydrocolloids such as, for example, polyvinyl alcohol, structurants, such as glucose, maleic acid and lactic acid, hair-conditioning compounds, such as phospholipids, for example soybean lecithin, egg lecithin and kephalins, and also silicone oils, protein hydrolyzates, more particularly elastin, collagen, keratin, milk protein, soybean protein and wheat protein hydrolyzates, condensation products thereof with fatty acids and quaternized protein hydrolyzates, perfume oils, dimethyl isosorbide and cyclodextrins, solvents and solubilizers, such as ethanol, isopropanol, ethylene glycol, propylene glycol, glycerol, diethylene glycol, ethoxybutanol and butoxyethanol and also benzyl alcohol, antidandruff agents, such as Piroctone Olamine and Zinc Omadine, other substances for adjusting the pH value, such as for example α- and β-hydroxycarboxylic acids, active principles, such as panthenol, pantothenic acid, allantoin, pyrrolidone carboxylic acids and salts thereof, plant extracts and vitamins, cholesterol, UV filters, consistency factors, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, pearlizers, such as ethylene glycol mono- and distearate, propellents, such as propane/butane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

Information on the other constituents of the colorants according to the invention can be found in the reference books known to the expert, for example Umbach, Kosmetik, 2nd Edition, Georg Thieme Verlag, Stuttgart/New York, 1995 and Kh. Schrader, Grundlagen und Rezepturen der Kosmetika, 2nd Edition, Hüthig Buch Verlag, Heidelberg, 1989.

Known processes may be used to develop the color on the keratin fiber.

In a preferred embodiment, the color is developed with atmospheric oxygen as sole oxidizing agent. This embodiment is particularly preferred when the group Y of the hybrid dye is derived from a melanin precursor or "air-oxidizable" primary and secondary intermediates or when the compositions contains melanin precursors and/or "air-oxidizable" oxidation dye precursors of the primary or secondary intermediate type. In the context of the invention, air-oxidizable compounds are compounds or dye precursors where oxidative development of the final color can be carried out solely with atmospheric oxygen, i.e. without using typical chemical oxidizing agents. Triaminobenzene derivatives are examples of such air-oxidizable compounds.

However, the use of a chemical oxidizing agent can be preferred in certain cases where the group Y of the hybrid dye derives from a melanin precursor or primary or secondary intermediates or where the composition contains melanin precursors and/or dye precursors of the primary or secondary intermediate type. The same also applies when the hair is not only to be colored, but also lightened. In such cases, particularly suitable oxidizing agents are presulfates, chlorites and, in particular, hydrogen peroxide or addition products thereof onto urea, melamine and sodium borate.

The preparation of the oxidizing agent is preferably mixed with the preparation containing the dye precursors immediately before colouring of the hair. The ready-to-use hair colouring preparation formed should preferably have a pH value of 5 to 11. In a particularly preferred embodiment, the hair colorant is used in a mildly alkaline medium. The application temperatures may be in the range from 15 to 40° C. and are preferably at the temperature of the scalp. After a contact time of ca. 5 to 45 and more particularly 15 to 30 minutes, the hair colorant is rinsed out from the hair to be colored. There is no need to wash the hair with a shampoo if a high-surfactant carrier, for example a colouring shampoo, has been used.

The preparation containing the dye precursors may be applied to the hair without premixing with the oxidation component, particularly where the hair is difficult to dye. After a contact time of 20 to 30 minutes, the oxidation component is applied, optionally after rinsing. After a further contact time of 10 to 20 minutes, the hair is rinsed and if desired washed with shampoo. In a first variant of this embodiment where the previous application of the dye precursors is intended to produce better penetration into the hair, the corresponding preparation is adjusted to a pH of about 4 to 7. In a second variant, oxidation with air is carried out first, the preparation applied preferably having a pH of 7 to 10. In the subsequent accelerated post-oxidation step, it may be preferred to use acidified peroxydisulfate solutions as the oxidizing agent. In one particular embodiment of this process, the final color is developed by repeated application of the preparation followed each time by oxidation with air. The preparation is preferably applied at intervals of about one day to about two weeks. Special shades can be obtained very selectively in this way.

Irrespective of which of the above-mentioned processes is used to apply the composition according to the invention, color development can be supported and increased by adding certain metal ions to the composition. Such metal ions are, for example, $Zn^{2+}$, $Cu^{2+}$, $Fe^{2+}$, $Fe^{3+}$, $Mn^{2+}$, $Mn^{4+}$, $Li^+$, $Ru^{3+}$, $Mg^{2+}$, $Ca^{2+}$ and $Al^{3+}$. $Zn^{2+}$, $Cu^{2+}$, $Mn^{2+}$, $Ru^{3+}$ and $Ca^{3+}$ are particularly suitable. In principle, the metal ions may be used in the form of a physiologically compatible salt. Preferred salts are the acetates, sulfates, halides, lactates and tartrates. The use of these metal salts enables color development to be accelerated and shades to be influenced as required.

Basically, oxidative development of the color may be carried out with atmospheric oxygen. As previously mentioned, however, a chemical oxidizing agent is preferably used. However, the oxidation colorant may also be applied to the hair together with a catalyst which activates oxidation of the dye precursors, for example by atmospheric oxygen. Examples of such catalysts include transition metal compounds, iodides, quinones or certain enzymes. Suitable enzymes are, for example, peroxidases which are capable of appreciably strengthening the effect of small quantities of hydrogen peroxide. One example of such an enzymatic process is the procedure whereby the effect of small quantities (for example 1% and less, based on the composition as a whole) of hydrogen peroxide is enhanced by peroxidases.

According to the invention, other suitable enzymes are those which directly oxidize the oxidation dye precursors with the aid of atmospheric oxygen, such as the laccases for example, or which produce small quantities of hydrogen peroxide in situ and thus biocatalytically activate the oxidation of the dye precursors. Particularly suitable catalysts for the oxidation of the dye precursors are the so-called 2-electron oxidoreductases in combination with the substrates specific to them, for example pyranose oxidase and, for example, D-glucose or galactose, glucose oxidase and D-glucose, glycerol oxidase and glycerol, pyruvate oxidase and pyruvic acid or salts thereof, alcohol oxidase and alcohol (MeOH, EtOH), lactate oxidase and lactic acid and salts thereof, tyrosinase oxidase and tyrosine, uricase and uric acid or salts thereof, choline oxidase and choline, amino acid oxidase and amino acids.

Accordingly, the present invention also relates to a process for coloring keratin fibers, more particularly hair, in which an oxidation colorant according to the invention is applied to the fibers together with an oxidizing agent and/or together with a catalyst for activating the oxidation process and, after a contact time, is rinsed off again with water or a water-containing surfactant preparation.

The present invention also relates to the use of a hybrid dye corresponding to formula (I) or a mixture of these hybrid dyes for coloring keratin fibers, more particularly human hair.

It has also been found that the hybrid dyes according to the invention are also eminently suitable for coloring human skin, more particularly for "tanning" human skin. Accordingly, the present invention also relates to the use of a hybrid dye of formula (I) or a mixture of these hybrid dyes for coloring human skin.

The following Examples are intended to illustrate the invention.

EXAMPLES

1. Syntheses 1.1. 4-(5,6-Dimethoxyindolin-1-yl)-phenylamine hydrochloride (hybrid dye A)

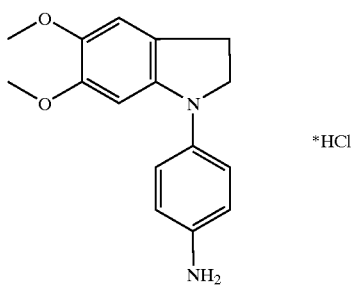

X derived from a melanin precursor (5,6-dimethoxyindoline)

Y derived from an oxidation dye precursor of the primary intermediate type (p-phenylenediamine)

S stands for an N structural element (=N of the five-membered ring of 5,6-dimethoxyindoline) which is the common constituent of the groups X and Y 1st Stage 6.3 g of 4-nitrofluorobenzene (0.045 mol) were stirred with 8.0 g of 5,6-dimethoxyindoline (0.045 mol) and 4.2 g of sodium hydrogen carbonate (0.050 mol) for 2.5 h at 80° C. in 50 ml of DMSO. After cooling, the mixture was poured onto ice, the precipitate was removed by filtration under suction and the product was dried in vacuo at 45° C. The intermediate product 5,6-dimethoxy-1-(4-nitrophenyl)-indoline was obtained in a yield of 65.6% (melting point: 176–179° C.).

2nd Stage 5,6-Dimethoxy-1-(4-nitrophenyl)-indoline was hyrogenated overnight with Pd (5%) on carbon in ethanol/water (8:2) in a shaking "duck". When the uptake of hydrogen had come to an end, 10% hydrochloric acid was added, the catalyst was filtered off and the remainder was concentrated to dryness. The residue was dried in vacuo at 45° C. The product 4-(5,6-dimethoxyindolinyl)-phenylamine hydrochloride was obtained in a yield of 84.9% (melting point: 143–145° C.).

1.2 6-(5,6-Dimethoxyindolin-1-yl)(3-pyridyl)amine hydrochloride (hybrid dye B)

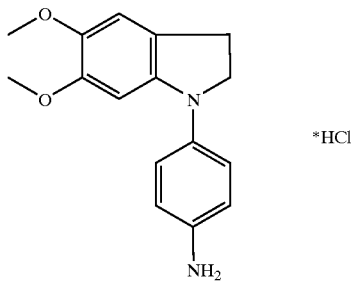

X derived from a melanin precursor (5,6-dimethoxyindoline)

Y derived from an oxidation dye precursor of the primary intermediate type (2,5-aminopyridine)

S stands for an N structural element (=N of the five-membered ring of 5,6-dimethoxyindoline) which is the common constituent of the groups X and Y 1st Stage 7.1g of 2-chloro-5-nitropyridine (0.045 mol) were stirred with 8.0 g of 5,6-dimethoxyindoline (0.045 mol) and 4.2 g of sodium hydrogen carbonate (0.050 mol) for 2.5 h at 80° C. in 50 ml of DMSO. After cooling, the mixture was poured onto ice, the precipitate was removed by filtration under suction and the product was dried in vacuo at 45° C. The intermediate product 5,6-dimethoxy-1-(5-nitro-(2-pyridyl)-indoline was obtained in a yield of 23.1% (melting point: 202–207° C.).

2nd Stage 5,6-Dimethoxy-1-(5-nitro-(2-pyridyl))-indoline was hyrogenated overnight with Pd (5%) on carbon in ethanol/water (8:2) in a shaking "duck". When the uptake of hydrogen had come to an end, 10% hydrochloric acid was added, the catalyst was filtered off and the remainder was concentrated to dryness. The residue was recrystallized with ethanol and active carbon. The product 6-(5,6-dimethoxyindolin-1-yl)-3-pyridylamine hydrochloride was obtained in a yield of 70.8% (melting point: 168–171° C.).

2. Coloring

A cream base with the following composition was first prepared [all quantities in g unless otherwise indicated]:

| | |
|---|---|
| Lorol ® techn.[1] | 4.0 |
| Texapon ® N 28[2] | 40.0 |
| Dehyton ® K[3] | 25.0 |
| Eumulgin ® B2 [4] | 1.5 |
| Stenol ® 1618[5] | 17.0 |
| distilled water | 12.5 |

[1]$C_{12–18}$ fatty alcohol (COGNIS)
[2]sodium lauryl ether sulfate (ca. 28% active substance; CTFA name: Sodium Laureth Sulfate) (COGNIS)
[3]fatty acid amide derivative of betaine structure with the formula R-CONH(CH$_2$)$_3$N$^+$(CH$_3$)$_2$CH$_2$COO (ca. 30% active substance; CTFA name: Cocoamidopropyl Betaine) (COGNIS)
[4]cetylstearyl alcohol containing ca. 20 mol EO (CTFA name: Ceteareth-20) (COGNIS)
[5]$C_{16–18}$ fatty alcohol (INCI name: Cetearyl Alcohol) (COGNIS)

The following hair coloring cream emulsion was then prepared on the basis of this cream:

| | | |
|---|---|---|
| cream base | 50.0 | |
| primary intermediate | 7.5 | mmol |
| secondary intermediate | 7.5 | mmol |
| Na$_2$SO$_3$ (inhibitor) | 1.0 | |
| (NH$_4$)$_2$SO$_4$ | 1.0 | |
| conc. ammonia solution to pH | 10 | |
| water | to 100 | |

The constituents were mixed together in the above order. After addition of the oxidation dye precursors and the inhibitor, the emulsion was first adjusted to pH 10 with concentrated ammonia solution and then made up to 100 g with water.

The color was oxidatively developed with 3% hydrogen peroxide solution as the oxidizing solution. To this end, 50 g of hydrogen peroxide solution (3%) were added to and mixed with 100 g of the emulsion.

The coloring cream was applied to ca. 5 cm long tresses of standardized, 90% gray but not specially pretreated human hair and left thereon for 30 minutes at 32° C. On completion of the coloring process, the hair was rinsed, washed with a standard shampoo and then dried.

The following compounds were used as further dyes/dye precursors: Oxidation dye precursors of the primary intermediate type

| | |
|---|---|
| K1 | resorcinol |
| K2 | 1-naphthol |
| K3 | 3-aminophenol |
| K4 | 2,4-diaminophenoxyethanol · HCl |
| K5 | 1,3-bis-(2,4-diaminophenoxy)-propane · 4 HCl · H$_2$O |
| K6 | 3-aminoaniline · 2 HCl |

The results of the coloring tests are set out in the following Table:

| Hybrid Dye | Other Dye Precursor | Color of Hair |
|---|---|---|
| A | K1 | Gray-turquoise |
| A | K2 | Turquoise blue |
| A | K3 | Gray-turquoise |
| A | K4 | Gray-turquose |
| A | K5 | Olive gray |
| A | K6 | Gray-turquoise |
| B | K2 | Dark blue |

We claim:

1. A method for coloring keratin fibers comprising applying to the keratin fibers a compound corresponding to formula (I):

X—S—Y  (I)

where
 X is a group derived from an indole or indoline derivative as a melanin precursor,
 Y is a group derived from
  an oxidation dye precursor of the secondary or primary intermediate type or
  an indole or indoline derivative as a melanin precursor; and
 S is a structural element which is common constituent of the groups X and Y, a direct bond or at least one spacer group.

2. A method for coloring human skin comprising applying to the skin a compound corresponding to formula (I):

X—S—Y  (I)

where
 X is a group derived from an indole or indoline derivative as a melanin precursor,
 Y is a group derived from
  an oxidation dye precursor of the secondary or primary intermediate type or
  an indole or indoline derivative as a melanin precursor; and
 S is a structural element which is common constituent of the groups X and Y, a direct bond or at least one spacer group.

3. A composition for coloring keratin fibers comprising formula (I):

X—S—Y  (I)

where
 X is a group derived from an indole or indoline derivative as a melanin precursor,
 Y is a group derived from
  an oxidation dye precursor of the secondary or primary intermediate type or
  an indole or indoline derivative as a melanin precursor; and
 S is a structural element which is common constituent of the groups X and Y, a direct bond or at least one spacer group.

4. The composition of claim 3 wherein Y is an oxidation dye precursor of the secondary or primary intermediate type.

5. The composition of claim 3 further comprising a substantive dye.

6. The composition of claim 3 wherein Y is a derivative of indole or indoline as the melanin precursor.

7. The composition of claim 3 further comprising a surfactant selected from the group consisting of anionic, zwitterionic, ampholytic, cationic and/or nonionic surfactants.

8. The composition of claim 3 further comprising a polymer selected from the group consisting of cationic, anionic, nonionic and/or amphoteric polymers.

9. The composition of claim 3 wherein X is 5,6-dihydroxyindoline or derivative thereof.

10. The composition of claim 3 wherein Y is p-phenylenediamine or derivative thereof.

* * * * *